United States Patent [19]

Barjon et al.

[11] Patent Number: 4,666,651
[45] Date of Patent: May 19, 1987

[54] HIGH ENERGY NEUTRON GENERATOR

[75] Inventors: Robert Barjon, Grenoble; Genevieve Breynat, Brignond, both of France

[73] Assignees: Commissariat a l'Energie Atomique, Paris; Centre Antoine-Lacassagne, Nice, both of France

[21] Appl. No.: 691,266

[22] Filed: Jan. 14, 1985

Related U.S. Application Data

[63] Continuation-in-part of Ser. No. 366,561, Apr. 8, 1982, abandoned.

[51] Int. Cl.[4] ............................................. G21G 1/10
[52] U.S. Cl. .................... 376/108; 376/117; 376/158; 376/151; 376/190
[58] Field of Search .............. 376/156, 158, 151, 190, 376/193, 194, 195, 108, 117

[56] References Cited

U.S. PATENT DOCUMENTS

| | | | |
|---|---|---|---|
| 2,816,242 | 12/1957 | Goodman | 376/194 |
| 3,107,210 | 10/1963 | Mallinckrodt | 376/151 |
| 3,860,827 | 1/1975 | Cranberg | 376/151 |
| 4,236,965 | 12/1980 | Lewis | 376/193 |
| 4,360,495 | 11/1982 | Bauer | 376/194 |

FOREIGN PATENT DOCUMENTS

| | | | |
|---|---|---|---|
| 1164280 | 10/1958 | France | . |
| 2386230 | 10/1978 | France | 376/194 |

OTHER PUBLICATIONS

J. A. Jungerman et al, Nuclear Instruments and Methods, vol. 89, pp. 167-172 (1970).
Roinel, Proc. of 1980 Int. Symp. (10/1/80) pp. 458-459.
Stein et al, Rev. Sci. Inst. vol. 45, No. 7, (7/74).
J. L. Romero et al, Nuclear Instruments and Methods, vol. 134 pp. 537-539 (1976).

Primary Examiner—Salvatore Cangialosi
Attorney, Agent, or Firm—Michael N. Meller

[57] ABSTRACT

A high energy neutron generator for use in neutron therapy.

The generator comprises a source for charged particles (preferably protons) with an energy level equal to at least 15 MeV, a target constituted by at least two lithium deuteride elements, whose thickness is such that under the impact of the charged particles, neutrons with an energy level equal to at least 15 MeV are largely produced in the forward direction, and target cooling means constituted by means for the circulation of a gas which does not chemically react with lithium deuteride. This generator may also comprise a collimator for defining an irradiation field of a patient and a permanent magnet able to deflect the charged particles not absorbed by the target towards a stopping unit positioned in and integrally formed with one wall of the collimator.

14 Claims, 2 Drawing Figures

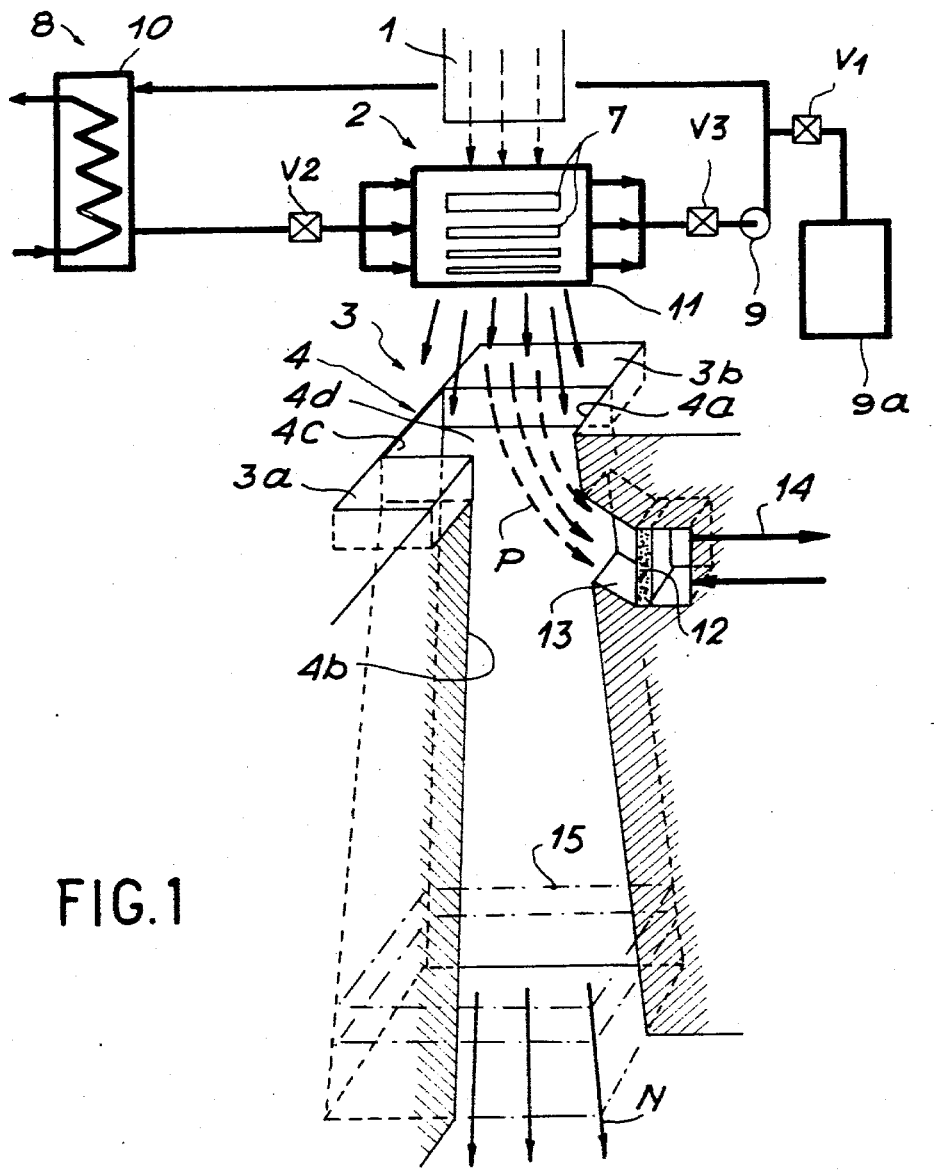
FIG.1
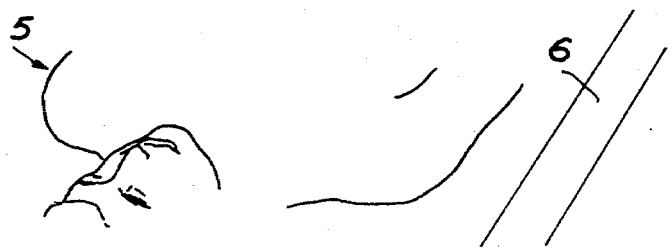

HIGH ENERGY NEUTRON GENERATOR

BACKGROUND OF THE INVENTION

This is a continuation in part application of U.S. patent application Ser. No. 366,561 filed Apr. 8, 1982, now abandoned.

The present invention relates to a high energy neutron generator, more particularly applicable in neutron therapy.

It is known that the neutron generators used at present in neutron therapy comprise either a particle accelerator (tandem or proton linear cyclotron), which bombards a beryllium target with its particles (protons or deuterium nuclei called deuterons) of energy between 15 and 60 MeV, or a particle accelerator, which bombards a tritiated target of deuterons of 150 to 500 KeV, or which bombards a hydrogenatable metal target ("autotarget", this target being regeneratable) with a mixture of deuterons and tritium nuclei (called tritons) of 150 to 500 KeV, so as to produce neutrons of energy equal to 15 MeV, which are very effective in neutron therapy.

However, particularly due to the nature and thickness of the targets therein, such generators do not make it possible to obtain high energy neutron beams which are as intense and as little contaminated by neutrons of energy below 15 MeV as would be desirable.

BRIEF SUMMARY OF THE INVENTION

The present invention aims at obviating these disadvantages.

It relates to a generator of fast neutrons only slightly contaminated by neutrons of energy less than 15 MeV, comprising a source of charged particles of energy equal to at least 15 MeV, a target made of lithium deuteride, and means for cooling said target, wherein said target comprises at least two elements placed in the path of said charged particles and separated from each other, the thickness of each of said elements being adjusted as a function of the average energy of the charged particles emitted from the source and the energy of the fast neutrons to be generated such that neutrons of energy equal to at least 15 MeV are emitted in the forward direction in response to the bombardment of said target by said charged particles, and wherein said target cooling means comprises means for circulating between and around said elements a gas which does not chemically react with lithium deuteride.

These elements can have different geometrical shapes.

The term "neutrons produced in the forward direction" is understood to mean neutrons emitted by the target in directions close to that of the incident charged particles.

The source of these charged particles also emits them with an energy defined as a function of the energy of the neutrons to be produced in the forward direction. Hereinafter values of the energy to be communicated to these particles will be given.

With regard to the choice of the target, since the incident charged particles are, for example, protons, the lighter the atoms are which constitute the target, the higher the quantity of neutrons emitted by direct interaction (predominant interaction for the energies in question) and the lower the quantity of lower energy neutrons resulting from secondary impacts.

Among the so-called light atoms (i.e. with atomic numbers below that of carbon), it is obviously preferable to choose those containing the most neutrons for forming the target.

It is necessary to eliminate from the list of materials which could be used deuterium and its normally gaseous and very light compounds such as $CD_4$ for installation and operating cost reasons (liquefaction is necessary in order to obtain an adequate density), tritium due to its price, radioactivity and difficulties of use, and helium due to the high value of the absorbed energy by a reaction (p, n) with helium. Thus, in the neutron generator according to the invention, a target made from lithium deuteride LiD (according to a preferred feature of the invention, $^7$LiD or natural lithium deuteride) is used because, for the same number of neutron targets and incident protons and for the same energy loss of the latter, the reaction (p, n) has a more than two times greater probability with the molecule $^7$LiD (but only approximately $1\frac{1}{2}$ times greater with the lithium 7 atom) than with a molecule of beryllium, heavy water or heavy paraffin.

Thus, using the generator according to the invention equipped with an LiD and $^7$LiD target, the quantity of neutrons obtained exceeds that obtained with the prior art generators using beryllium targets.

The charged particles can, for example, be deuterons, but are preferably protons. Thus, for producing neutrons of energy E equal to at least 15 MeV, it is possible to use a current of intensity I of protons of energy E or a current of intensity I/2 of dueterons of energy of 2E for the same power of the incident beam of protons or deuterons, direct interaction being favored at such energies. However, the cost of cyclotron, which forms the best source of protons or dueterons at the considered energy levels, is much more dependent on the energy to be passes to these particles (due to the fact that the energy is a rising function of the magnetic field and the dimensions of the cyclotron) than on the intensity of the current to be produced from the particles. According to a preferred feature of the invention, the particles are protons, so as to reduce the cost of the generator according to the invention.

The material (LiD) forming the target used in the invention has a limited thickness compared with that of the prior art targets and is designed such that few neutrons of energy below 15 MeV are produced in the forward direction under the impact of charged particles from the source. Therefore it is merely necessary to make this material sufficiently thick so that the incident charged particles which have not reacted with it, upon leaving the target still have an energy equal to at least 15 MeV when the charged particles are protons and at least 30 MeV when they are deuterons.

For example, with incident protons of 50 MeV, the LiD thickness is made such that the energy of protons which have not been stopped in the target is still at least 15 MeV upon leaving the target, which is then called "semi-thick".

By reducing the thickness of the target, compared with that of the prior art, it is also possible to reduce its heating by about 30%.

Preferably the thickness of the target is adjusted as a function of the average energy of the charged particles which the source is able to emit and the energy of the neutrons to be produced. It comprises approximately M elements consisting of pellets, each pellet having a different thickness and designed in such a way that the charged particles from the source lose ½ M of their energy. The pellets are spaced and arranged in order of decreasing thickness from the charged particle source.

It can be of importance to stop the partly delayed, incident charged particles which pass through the target. This is particularly the case in neutron therapy, where it is not desired that charged particles reach a patient during treatment. Thus, in known generators, the target is generally cooled by circulating of water to the rear of the target, which makes it possible to absorb a portion of the incident particles, such as protons which have not reacted with the target and were not slowed down or delayed by the latter. However, this arrangement has the disadvantage of partly degrading the energy spectrum of the neutrons produced by the target.

To obviate this disadvantage, the means for cooling the target in the generator according to the present invention comprise means for circulating a gas which does not chemically react with the material from which the target is made. This gas can be helium, whose effective diffusion section is particularly small for high energy neutrons.

According to another special feature of the present invention, the neutron generator also comprises means for eliminating parasitic particles which leave the target in the forward direction and which consist inter alia of charged particles which have not reacted with the target and neutrons from the target having an energy level below 15 MeV.

According to another preferred feature of the present invention, the parasitic particle elimination means comprise means for deflecting charged particles which have not been absorbed by the target to move them away from neutrons produced ahead, so that the latter are mainly neutrons with an energy level equal to at least 15 MeV.

According to another feature the neutron generator also comprises a collimator for defining an irradiation field.

The deflection means can deflect the charged particles not absorbed by the target to a wall of the collimator. A stopping unit equipped with a cooling system and and preferably substantially formed from carbon or helium, can be positioned in the collimator wall in order to stop the charged particles so defected.

According to another important feature, the deflecting means are able to produce a magnetic field for causing deflection. They may comprise a permanent magnet, which may at least in part be integrated with the walls of the collimator, which are able to form a magnetic circuit.

DETAILED DESCRIPTION OF THE DRAWINGS AND PREFERRED EMBODIMENTS

Figure 2:
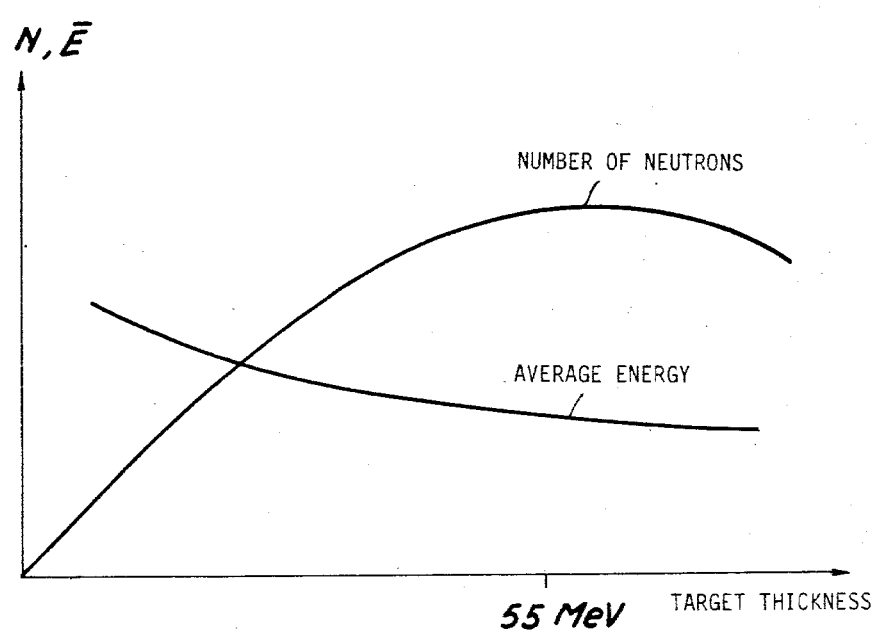

The invention is described in greater detail hereinafter relative to non-limitative embodiments and with reference to the attached drawings in which:

FIG. 1 diagrammatically shows an embodiment of the high energy neutron generator according to the invention for use in neutron therapy; and FIG. 2 shows curves making it possible to determine the thickness of the target included in said generator.

The generator of FIG. 1 comprises a source 1 of protons with an energy level equal to at least 15 MeV, which protons bombard a target 2, which then produces high energy neutrons N (of energy equal to at least 15 MeV). A permanent magnet 3 placed after target 2 deflects the protons P which have traversed the target without reacting with the latter in order to produce neutrons. A collimator 4 makes it possible to define an irradiation field for a patient 5 placed on a table 6. In order to be able to irradiate the patient 5 at the desired point, the generator and table 6 are displaceable by means (not shown), which are known in the art and do not form part of the invention.

Source 1 is a particle accelerator, such as a cyclotron, which supplies protons with an energy level of, for example, approximately 50 MeV. (In the case of a cyclotron, the protons can be transmitted to target 2 by known, but not shown, magnetic deflection means).

Target 2 is "semi-thick", the material from which it is made having a thickness such that the incident 50 MeV protons from source 1 which are not stopped by the target have, for example, lost in the latter at the most half of their energy. Thus, just before leaving target 2, the protons which have not yet been stopped by it can in fact be stopped and upon direct impact can produce neutrons with an energy level clost to 25 MeV. All the neutrons leaving the target in the forward direction consequently have an energy of at least approximately 25 MeV, well above 15 MeV. In this way it is possible to eliminate from the beam of fast neutrons N reaching the patient 5 a portion of the parasitic particles generally contained therein in the prior art generators and constituted by low energy neutrons (below 15 MeV).

The material forming target 2 is natural LiD or $^7$LiD. In addition to the advantages referred to hereinbefore, LiD also has a high melting point (above 600° C.).

In order to be appropriately cooled in a manner to be explained hereinafter, target 2 has several spaced LiD pellets 7. There are, for example, about 10 pellets, each of them having a different thickness and designed so that the protons from source 1 lose 1/20 of their intial energy upon passage through each pellet. Pellets 7 are arranged in order of decreasing thickness as from the proton source 1. In addition, the sum of the thicknesses of pellets 7 is adjusted as a function of the average energy (50 MeV) of the protons which the source 1 can emit and the energy of the high energy neutrons to be produced. By interaction with target 2, the protons from source 1 are consequently able to produce neutrons whose energy is at least approximately 25 MeV, because at most the protons have an energy loss of approximately $10 \times 1/20 \times 50 = 25$ MeV in target 2.

As lithium deuteride is normally in granular crystalline form, the particle size varying with the production method, the material is crushed and pulverized. Ingots are then made therefrom in a press at a temperature below 600° C. in order that there is no decomposition of the LiD. The ingots can then be cut up to form the aforementioned pellets.

Cooling means 8 for target 2 make it possible to circulate between the pellets 7 a gas which does not chemically react with LiD. The gas can be nitrogen or, preferably, helium (which is admittedly more expensive than nitrogen), which has little prejudicial influence on the energy of the neutrons produced from target 2 (and which can itself produce neutrons). The gas is recycled by means of a compressor 9, following optional cooling in a heat exchanger 10. The cooling means 8 also comprise a storage tank 9a, which can be isolated by a valve $V_1$. Target 2 is contained in a tight container 11, which can be isolated from the remainder of the cooling means 8 by two valves $V_2$ and $V_3$ and which can be easily dismantled and changed. Moreover, pipes for pressurized helium (max. pressure of 2.5 bars) can be more easily used with a mobile generator than water pipes, such as those used in the prior art neutron generators. In addition, as a result of not using a cooling system based on the circulation of water, the protective requirements are considerably reduced. Thus, in the case of high neutron fluxes, the radioactivity level induced in the water of prior art neutron generators is significant, as is the dissociation of water into hydrogen and oxygen as a result of radiolysis.

The incident protons P have an energy level well above 15 MeV after having participated in the neutronigenic or neutron-producing nuclear reaction and are slowed down in target 2 without being stopped therein, so that they have a range of at least 2 meter in air. However, when the neutron generator according to the invention is used in neutron therapy, target 2 is about 20 cm from collimator 4, which has a length of at most 120 cm. Therefore the patient 5 is at most 140 cm from target 2 and would therefore be reached by the protons P which are delayed, but not stopped by target 2 if protons P were not prevented from reaching the patient.

For the purpose of stopping protons P, it would be possible to use a thick plate made from a very heavy material such as tungsten (for limiting to the maximum the number of low evergy neutrons produced by the interaction of protons P with the plate), but this plate would lead to a deterioration of the spectrum of the useful high energy neutrons N when they passed through it. To obviate this disadvantage, it is preferable to move the protons P which are not absorbed by target 2, but are slowed down by the latter avay from the beam of high energy neutrons N by means of a magnetic field and to stop the protons in a trap, in the manner to be shown hereinafter. This also eliminates secondary low energy neutrons and γ photons, which protons P are liable to produce. Alternatively, it would obviously be possible to use electrostatic deflection means for protons P.

The magnetic field is produced by permanent magnet 3. An electro-magnet would be less onerous than the permanent magnet, but the latter is preferable as a result of its considerable reliability (i.e. a passive and substantially non-consumable element) and the ease with which it can be used.

Collimator 4, which is, for example, made from an iron-cadmium allow, has four walls 4a, 4b, 4c and 4d for defining a cylinder of square cross section and increasing cross-sectional dimensions (although the cross section can be any other geometric shape), its inlet facing target 2 and its outlet facing patient 5, thereby defining a field for the irradiation of the patient by the high energy neutrons N. For a better understanding of the drawing, collimator 4 is shown partially sectioned.

Permanent magnet 3 has two facing active parts 3a, 3b for forming the north and south poles of the magnet. These parts 3a, 3b are positioned in the vicinity of target 2, whilst being integrated into the walls of collimator 4. This arrangement of the magnet 3 is necessary because the magnet must be close to target 2 in order to ensure that an excessive air gap is not formed in view of the considerable divergence of the beam of protons P leaving target 2 (due to the multiple collisions of the protons with the nuclei of the target) and that a magnetic induction is exerted over a sufficiently long length to eliminate as rapidly as possible the protons P from the beam of therapeutic neutrons N.

The walls of collimator 4 make it possible to close the magnetic circuit of permanent magnet 3 by substituting iron for the iron-cadmium alloy forming these walls in the vicinity of the magnet.

The protons P not absorbed by target 2 are consequently deflected towards one of the walls (i.e., walls 4a). A stopping unit 12 arranged in a cavity 13 in wall 4a stops these protons P. The stopping unit 12 is of the Faraday cage type, is essentially formed from carbon in order to minimize the production of γ photons, and is provided with a cooling system 14 for eliminating the power given off during the bombardment of stopping unit 12 by protons P. The level of this power can rise to about 750 W for an intensity of 30 μA of protons P of energy equal to 25 MeV.

According to the prior art, certain known high energy neutron generators comprise equalizing filters, which compensate any anisotropy of the neutron fluence upon leaving the collimator, because there must be a uniform irradiation of the patient. This anisotropy is due to the thick targets used which diffuse the neutrons whilst changing their energy and their direction, so that the neutron fluence is greater at the edge of the beam of neutrons produced than in the center thereof. These equalizing filters absorb the low energy neutrons, but also significantly reduce the average energy of all the neutrons produced. They have a significant thickness and are made from highly hydrogenated materials, such as polyethylene or paraffin.

By deflectng the unabsorbed protons P which are generators of low evergy neutrons, the permanent magnet 3 reduces the number and thickness of the equalizing filters. Moreover, in the neutron generator according to the invention, the use of the "semi-thick" target 2 makes it possible to significantly reduce not only the quantity of low energy neutrons present in the therapeutic neutron beam, but also the anisotropy of the neutron fluence, due to the reduced thickness of the target 2 compared with the prior art. As a result, the equalizing filters can be eliminated to a considerable extent. Optionally such a filter 15 can be positioned near the outlet of collimator 4.

The high energy neutron generator described hereinbefore comprises a "semi-thick" target 2 made from natural lithium deuteride or $^7$LiD, a permanent magnet 3 for deflecting the protons P not absorbed by target 2, and optionally a much smaller equalizing filter 15, and is able to produce a high energy neutron flux which is only very slightly contaminated by parasitic partaicles (protons, low energy neutrons, γ photons). This modifies the depth irradiation efficiency and conditions the dose transmitted to the irradiated area of the patient in a manner favorable with respect to medical requirements. Compared with the prior art generators, it is possible to reduce the irradiation time by a factor of the order of 3 for the same proton stream bombarding the target.

Under these conditions the time taken to place a patient in front of the neutron beam is much higher than his irradiation time. It is then possible and economically advantageous to have an additional irradiation room, as compared with the presently known cases in which there is only one or at the most two irradiation rooms for one particle accelerator. in this case and in order to reduce the costs of the generator, the same cooling means 8 can be used for each of the targets 2 corresponding to the different irradiation rooms.

The high energy neutron generator according to the invention could also be used for producing high fluxes of fast neutron (approx. $10^{13}$ neutrons/cm$^2$/s) of approximately 15 MeV for studying the structural materials of nuclear reactors (by measuring the damage to test pieces caused by the slowing down of neutrons produced in deuteron-triton reactions and deuteron-deuteron reactions in such reactor).

Details on the calculation of the total thickness of the target are now given.

The total thickness L is defined by considering the two following parameters:

(a) total number of produced neutrons, (b) average energy of these neutrons, which are a function of the target thickness.

The calculation of the total number of emitted neutrons ismade as follows:

The attenuation of the incident beam of protons is calculated. If the current of protons impinging on the target is Io, the current Ix at a point x ($0 < x < L$) is given by the following equation:

$$Ix = Io\, e^{-\mu x}$$

in which $\mu$ is the attenuation coefficient, reciprocal of the total macroscopic interaction cross section:

$$\Sigma = N\, x \sigma \text{total} \qquad (1)$$

where:

$\Sigma$ is the total macroscopic cross section of DLi ($\Sigma$ of D plus $\Sigma$ of Li), N is the number of DLi molecules per unit volume, $\sigma$ total is the interaction cross section of DLi with protons ($\sigma$ of Li plus $\sigma$ of D) (microscopic).

Then, the umber of neutrons produced ahead is calculated.

The number of neutrons dn produced in the interval dx around x is:

$$dn = Io e^{-\mu x} \cdot (d\sigma/d\Omega)_{0°} \cdot N \cdot d\Omega \cdot dx$$

where:

$(d\sigma/d\Omega)_{0°}$ is the "forward" differential cross section at 0° for the (p, n) reaction on LiD N has the same meaning as in equation (1)

$d\Omega$ is the solid angle for the output of the neutron beam.

Some of the neutrons dn produced in the portion of the target will be attenuated in the rest of the target. Thus, dn has to be multiplied by the coefficient of attenuation $e^{-\mu'(L-x)}$ in which $\mu'$ is the attenuation coefficient for the neutrons of energy $E \approx N\sigma'$ total, $\sigma'$ total being the total interaction cross section of the neutron with the molecule DLi. Consequently, the number of produced neutrons is given by:

$$\int_0^L Io e^{-\mu x} \cdot \frac{d\sigma}{d\Omega} \cdot N \cdot e^{-\mu'(L-x)} \cdot d\Omega \cdot dx$$

$\mu$, $\mu'$ and $d\sigma/d\Omega$ varying with the energies of the neutrons and protons.

the calculation of the average energy of the neutrons is done with the "general formula of averages":

$$\overline{E} = \frac{\int n(E')\, E'\, dE'}{\int n(E')\, dE'}$$

In the particular case which is developped hereinabove, an with the same symbol meanings, one gets:

$$\overline{E} = \frac{\int E' \cdot Io e^{-\mu x} \cdot \frac{d\sigma}{d\Omega} \cdot e^{-\mu'(L-x)} dx}{\int Io e^{-\mu x} \cdot \frac{d\sigma}{d\Omega} \cdot e^{-\mu'(L-x)} dx}$$

Thus, one can calculate from those equations, curves of FIG. 2, which provide N and $\overline{E}$ as a function of the target thickness.

On FIG. 2, the target thickness is expressed in MeV. It is a convenient unit which is independent of the material used for the target: this target has a "length of E MeV" if the difference between the energy of a charged particle leaving the target and the energy of this particle impinging on the target is equal to E.

The target thickness is determined with the help of the given curves: the choice of N or E determines the thickness.

The total thickness of the target is the important parameter resulting from neutronic calculations, based on neutron performance. The division into elements is rather the result of technological considerations on a compromise between the target cooling and the mechanical resistance of the target.

An example of a neutron generator according to the present invention is now given:

This generator may comprise, for example, a set of 10 pellets of LiD, having a diameter of about 20 mm, shaped by isostatic pressing (at about 3,000 bars), and crimped in aluminium rings. For each ring, the difference between the outer radius and the inner radius is equal to 1 mm and each ring has a height equal to the thickness of the corresponding pellet. The thicknesses of the pellets are respectively 3.35 mm, 3.20 mm, 3.05 mm, 2.89 mm, 2.73 mm, 2.57 mm, 2.40 mm, 2.24 mm, 2.06 mm, 1.89 mm.

The spacing between the pellets is not crucial. The pellets may be separated from each other by a few millimeters (about 2 to 4 mm), e.g. 2.5 mm. They are cooled by a current of gaseous helium, at about 1.3 kg/cm$^2$, which is circulated by means of a turbine maintaining a flow of about 40 l/s.

A heat exchanger, cooled by liquid nitrogen, maintains the gaseous helium at a temperature of about $-30°$ C.

Protons of 55 MeV lose, on average, 4.4 MeV in each of the pellets. These pellets are arranged in order of decreasing thickness, the thickest pellet facing the incident beam of protons. The number of neutrons which are produced by a 12 $\mu$A beam of protons of 55 MeV is $2.10^{12}$ n/steradian.sec. in the direction of the beam of protons.

This example is particularly directed to medical applications. But it may be adapted to other energies of the protons, while keeping the same distribution for the energy of the produced neutrons.

For example, with protons of about 51 MeV, the first pellet (3.35 mm) is removed and the nine others are kept. With protons of about 46 MeV, the first two pellets (3.35 mm and 3.20 mm) are removed and the eight others are kept . . .

If the energy of the protons is increased, additional pellets are placed before the first one (3.35 mm), each additional pellet having a thickness such that the energy loss in each pellet is always about 4.4 MeV. This is obtained if each additional pellet has a thickness equal to the thickness of the preceding one (counted from the initial pellets) plus about the difference between the thicknesses of the two preceding pellets, i.e. plus about 0.15 mm to 0.20 mm. For example, if the energy of the protons is about 59 MeV, one additional pellet is placed before the first one (3.35 mm), the thickness of this additional pellet being about 3.5 mm (=3.35+0.15 mm).

The value of the current of protons may be reduced. In that case, the thickness of the pellets may be increased proportionnally to the reduction of the current. For example, if the current of protons is 6 μA (instead of 12 μA), 5 pellets may be used (instead of 10), the thickness of which being 6.55 mm, 5.94 mm, 5.30 mm, 4.64 mm and 3.95 mm respectively (sums, two by two, of the initial thicknesses), the pellets being ordered as explained above and the energy loss for the protons being then of about 8.8 MeV in each pellet.

Conversely, if the current of protons is increased, the thickness of the pellets should be reduced but such pellets are not easy to make. Then one may still use the ten initial pellets (3.35 mm ... 1.89 mm), their area of irradiation being increased proportionnaly to the value of the proton current. For example, with a current of protons of 24 μA, one may use the ten initial pellets with a diameter of about 28 mm (instead of 20 mm) for each of them so as to respect the technological limit of the maximum surface power.

What is claimed is:

1. A generator of fast neutrons only slightly contaminated by neutrons of energy less than 15 MeV, comprising a source of charged particles of energy equal to at least 15 MeV, a target made of lithium deuteride, and means for cooling said target, wherein said target comprises at least two elements placed in series in the path of said charged particles and separated from each other, the thickness of each of said elements being selected as a function of the average energy of the charged particles emitted from the source and the energy of the fast neutrons to be generated such that neutrons of energy equal to at least 15 MeV are emitted in the forward direction in response to the bombardment of said target from behind by said charged particles, and wherein said target cooling means comprises means for circulating between and around said elements a gas which does not chemically react with lithium deuteride.

2. A neutron generator according to claim 1, wherein said charged particles are protons.

3. A neutron generator according to claim 1, wherein said elements are made of a material taken from the group consisting of natural lithium deuteride and $^7$LiD.

4. A neutron generator according to claim 1, wherin the sum of the thicknesses of said target elements is selected as a function of the average energy of said charged particles bombarding said target and the energy of said neutrons to be produced, said elements being M in number and being in the form of pellets, each of said pellets having a different thickness such that said charged particles lose $\frac{1}{M}$ of their energy upon passage through each pellet, said pellets being spaced and arranged in order of decreasing thickness from said source of charged particles.

5. A neutron generator according to claim 1, wherein said gas is helium.

6. A neutron generator accroding to claim 1, further comprising means for eliminating charged particles not absorbed by said target from the stream of particles leaving said target in the forward direction.

7. A neutron generator according to claim 6, wherein said charged particle elimination means comprise means for deflecting said charged particles in a direction other than said forward direction.

8. A neutron generator according to claim 1, further comprising a collimator for defining an irradiation field.

9. A neutron generator according to claim 7, further comprising a collimator for defining an irradiation field, wherein said deflection means deflects said charged particles not absorbed by said target toward a wall of said collimator.

10. A neutron generator according to claim 9, further comprising a stopping unit arranged in said collimator wall and a cooling system for cooling said stopping unit, wherein said stopping unit stops said charged particles deflected by said deflecting means.

11. A neutron generator according to claim 10, wherein said stopping unit is made of a material taken from the group consisting of carbon and helium.

12. A neutron generator according to claim 7, wherein said deflection means are capable of producing a magnetic field for deflecting said charged particles.

13. A neutron generator according to claim 12, wherein said deflection means comprises a permanent magnet.

14. A neutron generator according to claim 9, wherein said deflection means comprises a permanent magnet at least partly integrally formed with the walls of said collimator, thereby forming a magnetic circuit.

* * * * *